United States Patent

Dussich

[11] 4,153,952
[45] May 15, 1979

[54] POLARIZED FACE SHIELD

[76] Inventor: Manlio V. Dussich, 383 N. Atlant. Ave., Apt. 406, Cocoa Beach, Fla. 32931

[21] Appl. No.: 853,405

[22] Filed: Dec. 9, 1977

[51] Int. Cl.² ............................................. A61F 9/00
[52] U.S. Cl. ............................................. 2/12; 2/6; 2/432; 350/159; 351/49
[58] Field of Search ............... 2/12, 6, 8, 427, 15, 2/431, 432, 425, 424, 9, 434; 350/159; 351/49

[56] References Cited

U.S. PATENT DOCUMENTS

| | | | |
|---|---|---|---|
| 2,422,287 | 6/1947 | Bernheim et al. | 351/49 X |
| 2,548,230 | 4/1951 | Molyneux | 2/8 |
| 2,688,900 | 9/1954 | Silverman | 350/159 X |
| 3,475,765 | 11/1969 | Zeltmann | 2/8 |
| 3,838,913 | 10/1974 | Schwarz | 351/49 X |
| 3,943,573 | 3/1976 | Budmiger | 2/8 |
| 3,944,346 | 3/1976 | Shindler | 350/159 X |
| 4,113,364 | 9/1978 | Dussich | 351/49 |

FOREIGN PATENT DOCUMENTS 935467  8/1963  United Kingdom ............................ 2/8

Primary Examiner—Werner H. Schroeder
Assistant Examiner—Andrew M. Falik
Attorney, Agent, or Firm—Duckworth, Hobby, Allen & Pettis

[57] ABSTRACT

A variable density polarizing attachment for shields combined with spectacles having polarizing lenses is provided along with a method of making variable density shields. A polarizing rotary disc is attached to standard shield adding optionally: polarized eye-protection and/or variable density shading with standard polarized lens' spectacles. The rotary disc is mounted on the inside of the shield and adjacent to standard polarizing spectacles' lenses. By rotating the disc the combination converts the sheidl to variable density. The set of snaps utilized to mount the rotary disc is modified to allow some air inside the shield, and/or to gyrate the disc.

4 Claims, 6 Drawing Figures

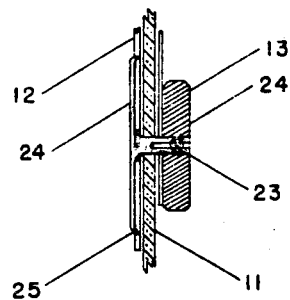
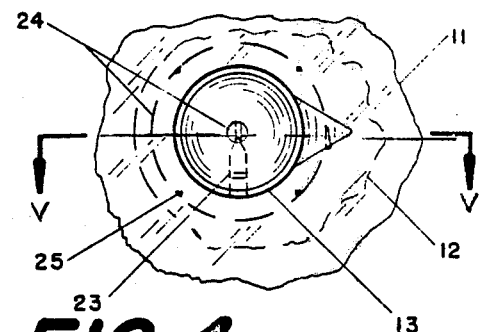
FIG. 5  FIG. 4
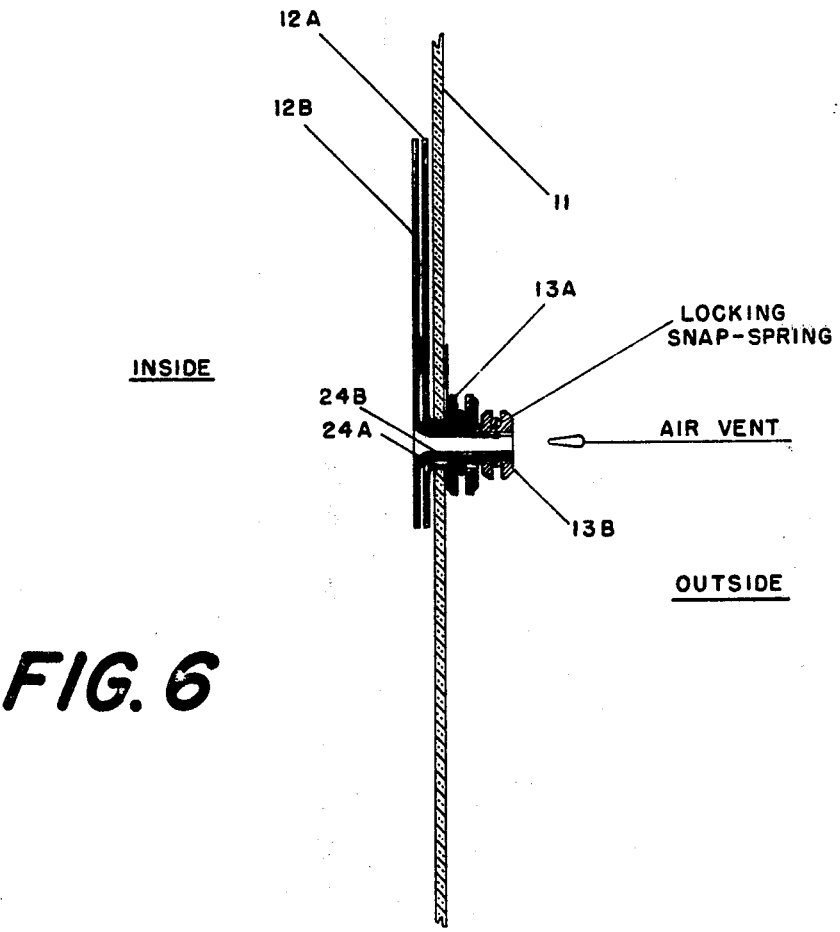
FIG. 6  MODIFIED

POLARIZED FACE SHIELD

BACKGROUND OF THE INVENTION

The present invention relates to rotary polarizing disc for attachment to existing shield in combination with spectacles having polarizing lenses, so that by varying the position of the attached polarizing disc, the transmission of light through the disc and the spectacle's lenses may be varied, controlled, set and utilized. There is no known record of shields for protective helmets having a simple, practical low cost hand operated polarizing disc attached to the inside of a clear helmet's shield used with polarizing spectacles or other items to reduce the hazard of blinding glare reflections and excessive brightness with one single day-nite shield. The prior art variable density shields and spectacles combination have been manufactured and sold in small quantities, but have not gained wide popularity due to complicated, costly and impractical methods and apparatuses. Typical prior art patents might be seen in the R. C. Haboush U.S. Pat. No. 3,159,844 which is electromagnetically controlled and not suited for sport helmets, while the J. H. Ash U.S. Pat. No. 825,288 does not use polarizing material. The present invention overcomes many of the prior art problems by producing the simplest methods and construction for manufacturing, assembling and operating such useful and safe combination of light shading variable range of density optionally available to a sportsman and other wearer with the economical factor of utilizing one single clear shield for both day and night use, also immediate needed shading variations availability as the weather and other variable conditions demands. With this invention the sportsman and others have the advantage of vision shading protection with variations from: A. No protection (Minimum shading)=full clear vision to, B. Medium protection with clear polarizing protection and to, C. Maximum protection of almost full shading in a matter of a few seconds, a safety factor of considerable magnitude. Optionally, by allowing some air to enter the inside through the disc's snap located at the nose and mouth area provides added breathing comfort and reduces the dangerous fogging possibility.

SUMMARY OF THE INVENTION

A variable density polarizing attachment for face shields to be used in conjunction with spectacles or the like having polarizing lenses or like material therein. The attachment consisting of a thin flex disc has a concentrically mounted snap (optionally vented) to be fastened to the inside of a helmet's face shield with its upper portion located in front of the eyes, and the lower portion partially extending beyond the shield's lower edge allowing it to be rotated at either directions and positioned at various density grades. The face shield is provided with an extra snap or the like to accomodate the polarizing attachment at a facially centralized location optionally with the shield mounted on the helmet or unmounted. A polarizing strip may be located in front of the eyes and to the inside of the shield in lieu of wearing polarizing spectacles. The snap-set is of special design with the outside front-part having a knob-arrow pointing combination to rotate the polarizing disc or a segment of it at the same time indicating the shading density grades.

BRIEF DESCRIPTION OF THE DRAWINGS

Other objects, features and advantages of the present invention will be apparent from the written description and the drawings in which:

FIG. 4 is a front view of a special pointing-knob assembly.

FIG. 5 is a sectional view taken along the line V—V in FIG. 4.

FIG. 6 is a sectional view of an embodiment of FIG. 4.

DESCRIPTION OF THE PREFERRED EMBODIMENTS

Figure 1:
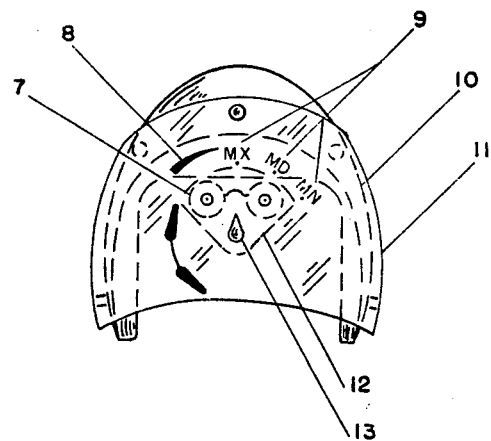
FIG. 1 is a front view of a helmet with a face-shield and disc's segment in place.

Referring now to FIGS. 1 through 6 of the drawings, a standard safety helmet 10 with a face-shield 11 optionally of polarized material is illustrated in FIG. 1 having a thin flexible segment of a disc 12 mounted on the inside on the helmet mounted shield 11. As shown, the segment 12 is facewise centrally positioned giving the eyes maximum shading protection with polarizing spectacles 7 in place. The pointing-arrow-knob 13 is pointing to "MX"=maximum density, one of the three density ref. marks 9, the others, "MD"=medium and "MN"=minimum. Also shown is density 'increasing-decreasing' ref. mark 8. Note that the rotating segment 12 being inside the helmet 10, is fully protected from the elements, such as rain - snow - icing, and dirt. The polarizing segment 12, is formed with horizontal polarizing axis and gives, from maximum shading as shown, to no shading when rotated out of the eye's field of view and without polarizing spectacles.

Figure 2:
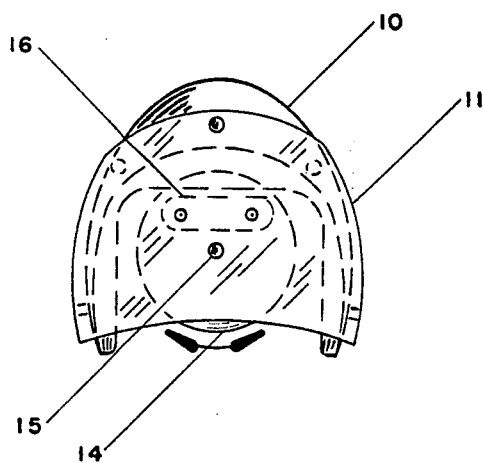
FIG. 2 is a front view of a helmet with shield and its windowed disc in place.

A rotating polarizing disc 14 with a window cut out 16 located in front of the wearer's polarized spectacles is shown in FIG. 2 mounted in the inside of shield 11 with a concentric and vented snap 15. The lower portion of the disc 14 is protruding sufficiently from the lower edge of shield 11 permitting finger actuation by side clamping and/or edge rotation in either direction. The opposite and parallel area of the window cut out 16 is squarely located where the polarizing axes are horizontal so that to obtain maximum density shading the rotating disc 14 will have to be gyrated 180 degrees from the position shown in FIG. 2 and with polarizing spectacles used. As shown, without polarizing spectacles, the wearer is obtaining maximum clear vision without any shading as a night rider would wish. Note that with these prompt and readily available options of maximum clear, to partial and maximum shading, there is no need for having two shields 11 and there is also no need to stop for the needed conversions since even the putting on and taking off of polarizing spectacles may be done with helmet on.

Figure 3:
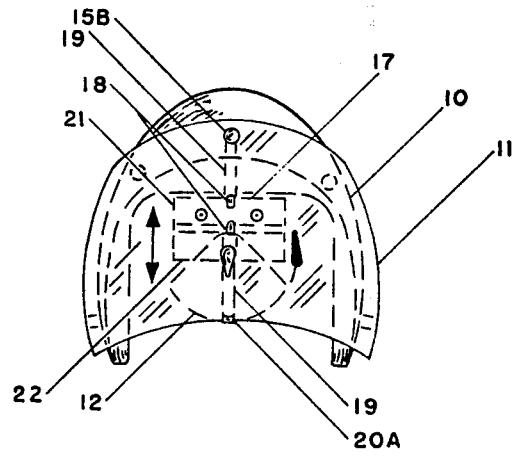
FIG. 3 is a front view of a helmet with shield and an up and down adjustable polarizing strip mounted on it.

A polarizing rectangular up and down adjustable thin strip 17 is shown in "up," shading position 21 in FIG. 3. This movable strip 17 is held to the inside of the face-shield 11 by means of two paper clamps 18 holding one elastic strip 19 anchored to the outside of the upper center snap at B-location and another lower elastic strip 19 anchored to A-location onto the shield 11 lower edge with hook 20. With the polarizing strip 17 in a "down" or no shading position 22, the hook 20 may be removed from the A-location, and relocated onto the upper and center snap at B-location. This "up and down" adjustable polarizing strip 17 is held flat against the inside curved surface of shield 11 and is conveniently and economically used in lieu of polarizing spectacles. The segment 12 is ready and available for fast variable density grades and settings and is shown positioned at "clear-no shading" area in FIG. 3.

The special pointing-knob 13 is detailed with a front view in FIG. 4 which shows how said knob is locked with the flanged driving shaft of pronged member 24 by means of a set screw 23. The pronged member 24 is pressed firmly into the polarizing segment 12, the driving and optionally parted shaft's end passing through the face-shield 11 is shown in section V—V FIG. 5. Note the four prongs 25 imbedded into item 12.

The "double segment-knob" embodiment is shown in FIG. 6 as: section V—V of FIG. 4 (modified). Similar segments to item 12 are listed as 12A and 12B and are illustrated having telescopic tubular flanged shafts 24A and 24B locked together in place onto the face-shield 11 with knobs 13A and 13B, which are vented allowing air to enter the breathing area inside the protective sportman's helmet. Optionally each segment is moulded to a splined telescopic shaft for a plastic keyed knob to engage with. The knob is locked laterally to the shaft with a knob and shaft engaging snap-spring. The double segment 12A and 12B allows the use of two polarizing elements with the user not having to wear spectacles, and without mounting a second polarizing segment to the shield.

I claim:

1. A variable density polarizing attachment for face-shields having polarizing material therein comprising in combination:
   polarizing spectacles;
   a face shield;
   a polarizing segment fastened to a frontal knob's shaft mounted onto said shield;
   means for mounting said segment to said shield's rear side in predetermined position adjacent to the polarizing spectacles with the frontal knob engaging the rear of said segment whereby rotation of said knob causes the light transmission through said spectacles to be varied.

2. The apparatus in accordance with claim 1, in which said polarizing segment includes first and second members, said first member being a polarizing member fixedly fastened onto a flanged shaft of said second member.

3. The apparatus in accordance with claim 2, in which said second member is mounted and positioned through an opening in a polarizing shield and together with first member is locked from the other side of said shield, with said knob.

4. A method of attaching a variable density polarizing attachment for face-shield therein comprising the steps of:
   making an opening on a face-shield at a predetermined position;
   inserting an outer member of a telescopic shaft supporting its frontal polarizing segment, through said shield's back side opening;
   inserting an inner member of a telescopic shaft supporting its rear polarizing segment through an outer member of a telescopic shaft;
   mounting and locking an outer member of a telescopic shaft with a larger knob member against a frontal face-shield with lateral and rotational freedom for its polarizing segment;
   mounting and locking an inner member of a telescopic shaft with a smaller knob member against a locked larger knob member with lateral and rotational freedom for its polarizing segment;
   whereby the larger and smaller knobs can be rotated individually to set said front and rear segments to cause variable density polarizing shades to be formed in combination.

* * * * *